United States Patent [19]

Bing

[11] 4,374,061
[45] Feb. 15, 1983

[54] MEANS AND METHODS FOR PURIFYING C1Q, C1R AND C1S

[75] Inventor: David H. Bing, Brookline, Mass.

[73] Assignee: Center For Blood Research, Inc., Boston, Mass.

[21] Appl. No.: 287,139

[22] Filed: Jul. 27, 1981

[51] Int. Cl.³ .............................................. C07G 7/00
[52] U.S. Cl. ............................ 260/112 R; 260/112 B; 424/85
[58] Field of Search ...................... 260/112 R, 112 B; 424/101, 85

[56] References Cited

U.S. PATENT DOCUMENTS

| | | | |
|---|---|---|---|
| 3,959,079 | 5/1976 | Mareschi | 195/63 |
| 3,959,080 | 5/1976 | Dieter | 195/63 |
| 3,995,018 | 11/1976 | Sjoquist | 424/1.5 |
| 4,224,439 | 9/1980 | Ayers | 536/32 |
| 4,239,743 | 12/1980 | Sedlacek | 424/1 |

OTHER PUBLICATIONS

Assimeh, S. N. et al, J. Immunology, vol. 113, pp. 225-234, 1974.
Bing, D. H., Methods Enzymol, vol. 34, 731-746, 1974.
Bing, D. H. et al, Protides Biol. Fluids Proc. Colloq., vol. 23, 551-557, 1976.

*Primary Examiner*—Allan Lieberman
*Assistant Examiner*—P. Short
*Attorney, Agent, or Firm*—Wolf, Greenfield & Sacks

[57] ABSTRACT

A novel resin is provided for use in chromatography to enable purification of plasma proteins C1q, C1r and C1s from Cohn Fraction I and other materials. An improved method results in obtaining substantially all of these materials from Cohn Fraction I or other media. The components of complement thus obtained are highly purified and retain full biological activity.

8 Claims, 1 Drawing Figure

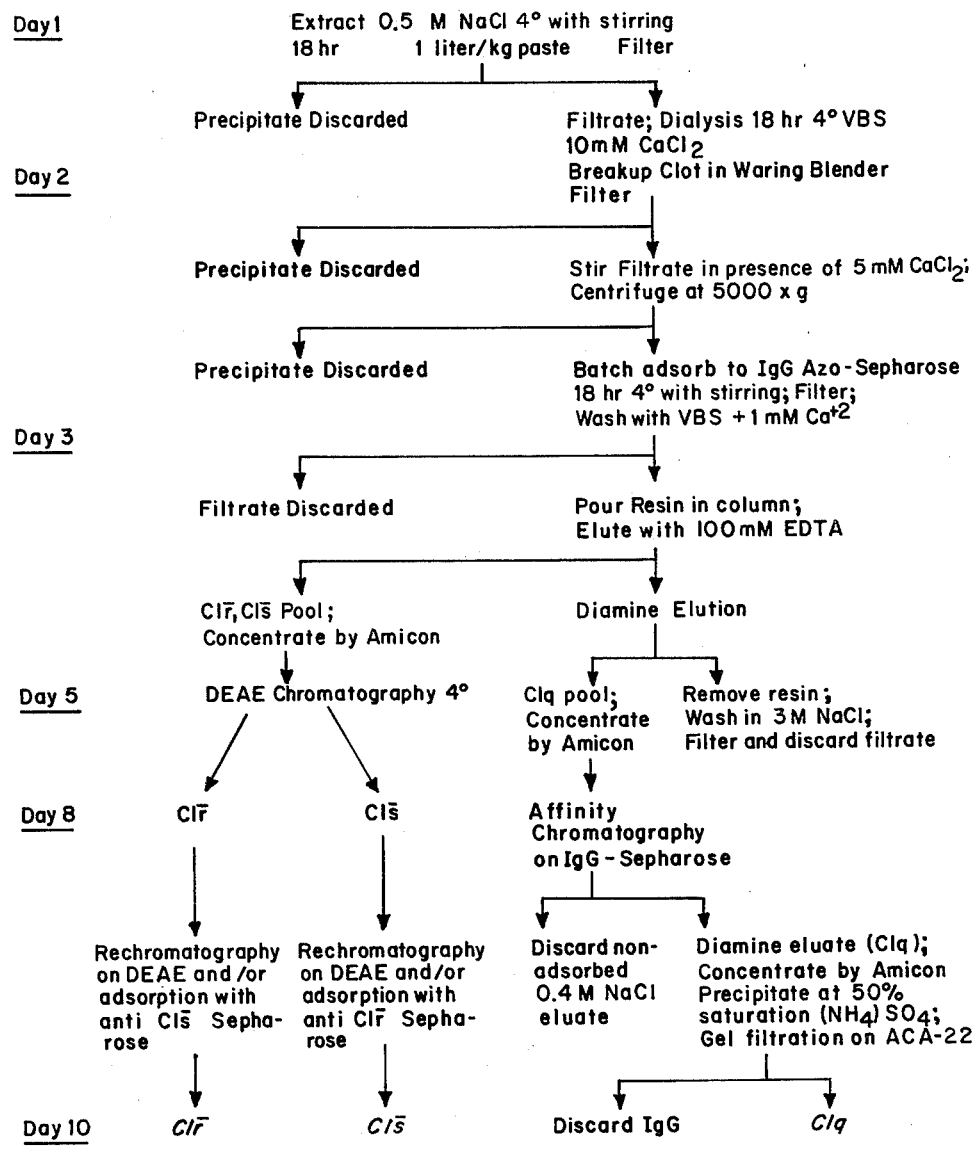

MEANS AND METHODS FOR PURIFYING C1Q, C1R AND C1S

BACKGROUND OF THE INVENTION

The first component of complement is made up of three distinct plasma glycoproteins, C1q, C1r and C1s. These glycoproteins form a macromolecular calcium ion dependent complex with a molar ratio of 1:2:2. This complex circulates in vivo as a proenzyme which is activated on binding to immune aggregates or insolubilized IgG.

Purification of the three proteins C1q, C1r and C1s has been accomplished in the past by a series of steps which include precipitation of C1 complex at low ionic strengths or by polyethylene glycol, disassociation of C1 in the presence of ethylene diamine tetraacetic acid and resolution of the C1 subcomponents by column chromatography. Final purifications are then carried out. Other procedures include absorption of C1 to immune precipitates followed by elution and subsequent resolution by ion exchange chromatography. It has previously been demonstrated that C1r and C1s subcomponents can be dissociated from C1q by ethylenediamine tetraacetic acid (EDTA) when the C1 complex is bound to IgG-Sepharose resin, (S. N. Assimeh, D. H. Bing and R. H. Painter, J. Immunol. 113, 225–234 (1974); D. H. Bing, J. M. Andrews, F. L. Suddath and R. Spencer, in "Protides of Biological Fluids," H. Peeters, ed., Pergamon Press, New York, 1975, pp. 551–557; W. P. Kolb, L. M. Kolb and E. R. Podack, J. Immunol. 122, 2103–2111 (1979); K. Takahashi, S. Nagasawa and J. Koyama, FEBS Letters 55, 156–160 (1975)). Improved resolution occurred when the IgG was separated from the resin by a spacer which was a p-benzamidoethylamine linkage.

The cold water-ethanol process, or Cohn Process, for the purification of plasma proteins is used widely in the preparation of serum albumin and immune globulins. There have been reports in which Cohn Fractions have been used as starting material for the preparation of a number of materials; however, Cohn Fractions have been found of little use as a starting material for the preparation of highly purified, functionally active complement proteins, perhaps due to the instability of this group of proteins to the conditions used during fractionation. Strong, (L. E. Strong, in "Encyclopedia of Chemical Technology," Vol. 2, R. E. Kirk and D. F. Othmar, eds., Interscience Encyclopedia, New York, 1948, pp. 1–29), in his review of Cohn methodology, indicated that C1 could be found in Fraction III and recently, Granier et al, (C. Granier, A. Faure, R. Tavernier and M. Steinbuch, Prep. Biochem. 9, 281–291 [1979]), reported the isolation of C1q from the euglobulins in this fraction. Furthermore, Lepow and Ratnoff, (O. D. Ratnoff and I. H. Lepow, J. Exp. Med. 106, 327–343 [1957]), suggested that Fractions I and III were a source of the proenzyme form of C1.

Cohn Fraction I has not normally been used for commercial preparations in the past. In fact, the material is often considered a waste material suitable only for research use.

Yet, it has been difficult to obtain highly purified and active subcomponents of the first component of complement C1q, C1r and C1s which are known to be useful in the clinical testing for immune complexes or investigations of the biochemical activities of complement proteins in plasma or serum.

SUMMARY OF THE INVENTION

It is an object of this invention to provide a resin particularly suitable for use in separation of subcomponents of complement from fluids.

A still further object of this invention is to provide a resin in accordance with the preceding object which can be formulated for use in affinity chromatography.

Still another object of this invention is to provide methods for separating C1q, C1r and C1s from fluids such as Cohn Fraction I after which the various subcomponents can be separated from each other.

Still another object of this invention is to provide methods for production of the resins of the present invention which methods include modification of immunoglobulin to form an affinity resin.

According to the invention, a resin comprises a protein bound to an insoluble polysaccharide. The protein is selected from the class consisting of IgG, IgM, and Fc fragments of IgG or IgM which contain the binding region for complement component C1q, thereof and therefore capable of separating C1q bound to C1r and C1s from fluids such as Cohn Fraction I, plasma and other materials. The protein has linked thereto at one or more histidine sites an organic arm through an azo bond and the arm to the polysaccharide at a hydroxyl site through an ether or imino bond.

The arm has the following formula when linked to the protein B:

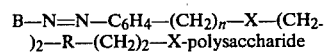

n = 1, 2, 3 or 4
X = O or NH
R = SO$_2$ or CH$_2$NHCH$_2$ or:

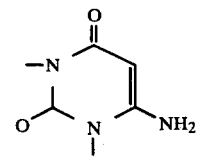

or:

or:

B = IgG, IgM or Fc fragments.

In the preferred embodiment, the IgG or IgM is attached to agarose polymer by an azo-benzyloxyethylsulfono-ethoxy arm portion.

Preferably the resin of this invention is synthesized by taking a polysaccharide such as a Sepharose material and activating to react with a diallene. The arm is then made with the use of an aromatic nitro compound which is then formed into a diazonium compound and coupled to a protein at histidine sites thereof which protein can be the IgG, IgM or Fc fragments of IgG or IgM.

In the method of this invention, Cohn Fraction I is treated by obtaining purified C1q, C1r and C1s preferably within twenty-four hours of fractionation. The subcomponents of complement are obtained at a temperature of about 4° C. Speed is used to avoid the possibility of inactivation due to proteolysis or other inactivation processes. Affinity chromatography is used and the subcomponents are separated from each other after first obtaining them from Cohn Fraction I.

It is a feature of this invention that the subcomponents of complement can be obtained with substantially the known biological activities of these materials. The materials are the same as C1q, C1r and C1s obtained from clotted plasma or serum in conventional steps. There is no evidence of any degradation. The materials are suitable for use in tests such as immune complex assays or investigations of the biochemical activities of the complement proteins. Complement as used herein is that obtained from human blood and present in human blood. However, the same techniques and materials can be used in connection with obtaining subcomponents of complement other than that of human complement such as other mammalian complement. Thus C1q, C1r and C1s can be obtained from mammalian fluids of cow, horse, goat, pig and the like using plasma, serum, blood, or fractions thereof as starting materials.

DESCRIPTION OF PREFERRED EMBODIMENTS

The preferred resin of this invention used as an affinity resin can have as a background any of IgG immunoglobulin G materials, immunoglobulin M materials or Fc fractions thereof. Immunoglobulin G is known in the art as a normal constituent of mammalian blood. It is a four chain polypeptide consisting of two identical heavy (H) and two identical light (L) chains with molecular weights of approximately 50,000 and 25,000, respectively. The properties of human IgG are summarized in the following table:

| Molecular Formula | $\lambda_2\gamma_2$ or $\kappa_2\gamma_2$ |
| --- | --- |
| Subclasses | $IgG_1$, $IgG_2$, $IgG_3$, $IgG_4$ |
| Subclass Light Chain | $\lambda$ or $\kappa$ |
| Subclass Heavy Chain | $\gamma_1$, $\gamma_2$, $\gamma_3$, $\gamma_4$ |
| Heavy Chain Allotypes | $G_m$ (about 20 different known) |
| Molecular Weight | 150,000 |
| Sedimentation Constant ($S_{20}$) | 6.6S |
| Carbohydrate Content | 3% |
| Serum Level (adult average) | $1250 \pm 300$ mg/100 ml |
| Percentage of Total Serum Immunoglobulins | 75–85% |
| Total Circulating Pool | 494.4 mg/kg of body weight |
| Half Life (in vivo) | 23.0 days |
| Rate of Synthesis | 33 mg/kg body weight/day |
| Biological Properties | antibody activity; binding to complement component C1q |

The light ($\lambda$ or $\kappa$) chains are covalently linked to the heavy ($\gamma$) chains by an interchain disulfide bond. There are two additional intra chain disulfide bonds in the light chains and four in the heavy chains.

The light chain consists of approximately 220 amino acid residues. In the amino terminus of light chain, consisting of 110 amino acids, the amino acid sequence and composition varies depending on the antigenic specificity of the antibody. For this reason it is called the variable region (VL). The carboxy terminus containing the other 110 amino acids is constant within a given subclass of light chain and is thus called the constant region (CL). All K chains have an identical constant region which is different from the constant region of $\lambda$ light chains.

The heavy chain consists of approximately 440 amino acids. The amino terminus also contains a 110 amino acid variable region but the carboxy terminus consists of three constant regions (C$\gamma_1$, C$\gamma_2$ and C$\gamma_3$). A given subclass and allotype of a heavy chain contains identical constant regions, but the variable region (VH) varies depending on the antigenic specificity of the antibody. The carbohydrate is attached to one of the constants (C$\gamma_2$) regions. A schematic diagram of IgG$_1$ is shown below:

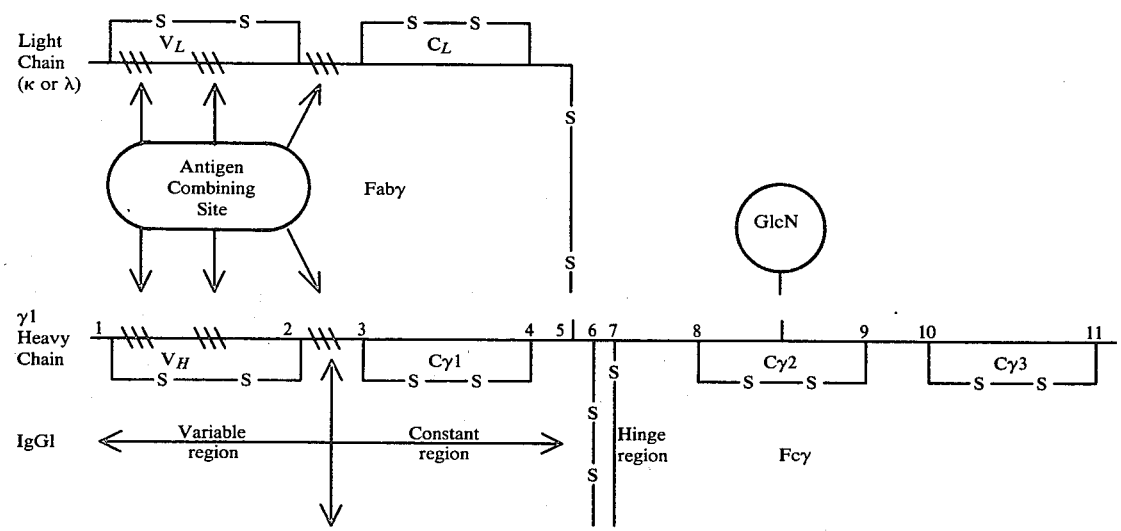

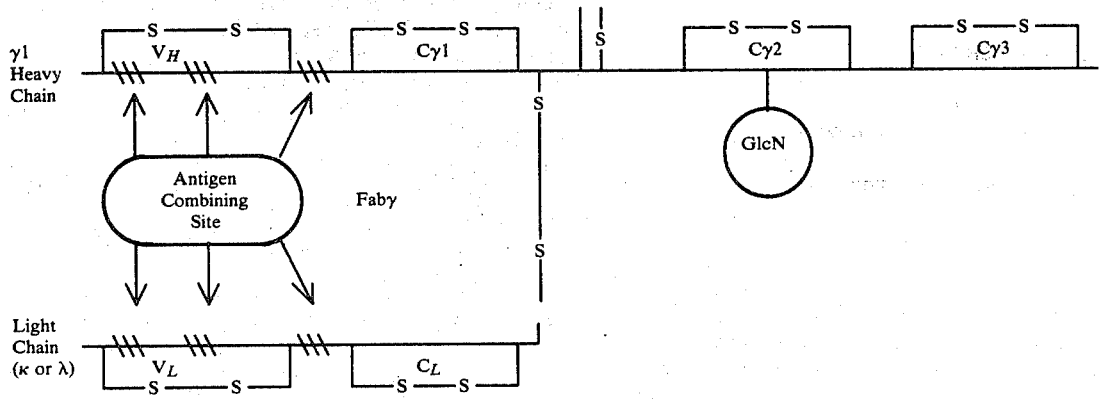

IgG$_2$ IgG$_3$ and IgG$_4$ have identical structures except the heavy (H) chain are $\gamma_2$, $\gamma_3$ and $\gamma_4$, respectively. There is one other class of immunoglobulin which binds the complement component Clq. This is called immunoglobulin M(IgM). It is a polymeric immunoglobulin with structural features similar to IgG. IgM is a distinct protein and is not a polymer of IgG. Immunoglobulin G (IgG) isolated from normal plasma is a mixture of all subclasses of IgG although there is not equal amounts of all subclasses in normal blood. On the average the relative distribution of the subclasses IgG 77%, IgG$_2$ 14%, IgG$_3$ 6% and IgG$_4$ 3%. IgG prepared from pooled normal human plasma collected at the American Red Cross is used in the following examples. Any IgG can be used and the source is not a unique feature.

The polysaccharide which is linked to the immunoglobulin or fraction is preferably a polygalactose although other polysaccharides can be used. The polysaccharide must be a resin that has good flow properties such as (20–40 cm/hr) at hydrostatic pressures two to three times the height of the bed of the column to be used. Any polysaccharide which can be converted to a bead form would be suitable for use in preparing the resin of the present invention. Agarose is particularly desirable and is available from several companies such as Pharmacia Fine Chemicals of Piscataway, N.J. under the trade names Sepharose 4B, Sepharose 6B, Sepharose CL4B, Sepharose CL6B and Sephadex; BioRad of Richmond, Calif. under the names BioGel A 0.5, BioGel A 1.5, BioGel A 5; and Marine Colloids of Rockland, Me. under the name Seakem AC Beads.

In the preferred embodiment, from 5 to 10 mg of IgG to resin is used.

The procedure for bonding the polysaccharide resin to the immunoglobulin is preferably to couple a diallene to the polysaccharide such as Sepharose. Divinylsulfone is the preferred diallene but other diallenes as for example those noted below can be used:

| Name | Formula | Advantage | Disadvantage |
|---|---|---|---|
| Diallylamine | $(H_2C{=}CH{-}CH_2)_2NH$ | solubility | severely toxic |
| 1,3-Diallyl-6-amino uracil | $CH_2{=}CH{-}N\underset{O}{\overset{O}{\|}}\ldots NH_2$, $N{-}CH{=}CH_2$ | solid, soluble | theoretically cleaved by nucleases |
| N,N′—Diallyl-tartardiamide | $[{-}CH(OH)CONHCH_2{-}CH{=}CH_2]_2$ | solid, soluble could be used with polyacrylamide | can be cleaved by peptidases |
| 1,3-Diallylurea | $H_2C{=}CHCH_2NHCONHCH_2CH{=}CH_2$ | solid, very soluble cycolize during synthesis | will tend to |
| Divinyl Sulfone | $CH_2{=}CHSO_2CH{=}CH_2$ | ether linkage not readily cleaved by any plasma protease or enzyme | toxic |

An excess of divinylsulfone is preferred and in the range of 10 to 30% excess. The reaction proceeds for preferably twenty to thirty minutes starting at room temperature with stirring to dissipate the exothermic heat. The reaction preferably takes place in a solvent of 1 M sodium bicarbonate aqueous solution buffered to about pH 11. The reactants are dissolved and the pH range preferably maintained between 10 and 12. Filtering is then carried out to remove the unreacted divinylsulfone. p-nitrobenzyl alcohol is then used. Other aromatic nitro compounds which can be used instead of the p-nitrobenzyl alcohol include the following:

m or o nitrobenzyl alcohol
p or o nitrophenylethyl alcohol
p nitrophenylethyl amine
4(p-nitrophenyl)-1-butanol In theory any compound of general formula as follows could be used:

$$NO_2-C_6H_4-(CH_2)_n-D$$

where n=1, 2, 3, 4
beyond n=4, it would not be soluble
D=OH or NH$_2$

Both groups will react with the allene. With the amine, the reaction would probably go well at pH 9 or 10.

Because of the ease of using the NO$_2$ function, it is the group of choice. Use of an amino function that is blocked would require devising conditions to deblock.

The reaction can take place in any non-reactive solvent up to the solubility of the p-nitrobenzyl alcohol. Preferably up to 50% dimethyl formamide at reaction conditions of room temperature for at least seven hours up to twenty-four or more hours are used. The reactants are then filtered and washed and an amino group formed by reducing the nitro groups with a reducing agent such as sodium dithionite. The concentration of the dithionite is preferably 0.2 M in solution with a time of about an hour being used at 40° C.

The arm formed is activated by converting the amino group formed to a diazonium ion by the addition of nitrous acid preferably formed in situ at from 0° to 4° C. Above 4° C. the diazonium ion can be destroyed. This is then coupled to the protein at a histidine residue by reacting at a pH of from 8 to 9 and preferably 8.5 to enhance coupling at the desired site. Up to 80% or better of the histidine sites are coupled by this step.

Preferably the purification of C1q, C1r and C1s which are subcomponents of the first component of the complement is obtained from Cohn Fraction I. Cohn Fraction I is known in the art. It is the precipitate which is formed upon addition to plasma at 0° C., 8% ethanol at an ionic strength of 0.14, temperature of −3° C. and protein concentration of 5.1%. Cohn Fraction I contains the following known proteins:
  C1q (and the entire C1 component)
  cold insoluble globulin or plasma fibronectin
  fibrinogen
  factor VIII or antihemophilic factor
  factor XIII
  properdin
Minor amounts of the following are also found:
  albumin
  α$_2$-macroglobulin
  immunoglobulins (IgG, IgA, IgM)
  factor VII
  plasminogen
  C3
  C4
  C5
  C8
  amylase
  lysozyme
  unknown β globulin
A precise definition of Cohn Fraction I is found in the following reference: L. E. Strong In Encyclopedia of Chemical Technology, Vol. 2 (R. E. Kirk and D. F. Othmar, eds.), Interscience Encyclopedia, New York, 1948, pp. 1-29.

Other fluids from which C1q has been retrieved by the resin and method of this invention include plasma, serum, and tissue culture media harvested from cells which synthesize C1q.

In assaying for the material obtained by specific examples of this invention, assays for C1 activity are carried out with EAC4 prepared from guinea pig serum and EA as described Mayer (E. A. Kabat and M. M. Mayer, "Experimental Immunochemistry," 2nd edn., Charles C. Thomas, Springfield, Ill., 1961). Functionally pure C2 and CEDTA were prepared as described by Nelson et al (R. A. Nelson, J. Jenson, I. Ggigli and N. Tamura, Immunochemistry 3, 111-135 [1966]). The assay for C1 was as described by Rapp and Borsos (H. J. Rapp and T. Borsos, "Molecular Basis of Complement Action," Appleton-Century-Crofts, New York, 1970), except volumes were reduced by one-fifth to conserve reagents. To reconstitute C1, the following conditions were used: dilutions of C1q, C1r and C1s were mixed in equal volumes in the presence of 0.15 mM CaCl$_2$-1.0 mM MgCl$_2$. After incubation for 10 minutes at 32° C., these mixtures were assayed for C1 activity as described above. C1r and C1s were assayed for esterase activity verses NZTP in a Gilford 240 spectrophotometer as described by Bing (D. H. Bing, in "Methods in Enzymology. Affinity Methods Part B," W. B. Jakoby and M. Wilchek, eds., Academic Press, New York, 1974, pp. 731-746). NPGB was used to titrate C1r in a Cary 118C spectrophotometer as outlined by Andrews and Baillie (J. M. Andrews and R. D. Baillie, J. Immunol. 123, 1403-1408 [1979]). Where indicated, the biuret method described by Lowry et al (O. H. Lowry, N. J. Rosebrough, A. L. Farr and R. J. Randall, J. Biol. Chem. 193, 265-275 [1951]) was used to determine protein concentration and bovine serum albumin was used to construct a standard curve. For purified proteins, the following extinction coefficients ($E_{280}^{1\%}$) were used: C1q=6.8, (G. Gigli, R. R. Porter and R. B. Sim, Biochem. J. 157, 541-548 (1976), C1r=9.4 (R. B. Sim, R. R. Porter, K. B. Reid and I. Gigli, Biochem. J. 163, 219-227 [1977]) *Buffers.* Veronal buffered saline (VBS) pH 7.4, 0.15 ionic strength and VBS containing 0.15 mM CaCl$_2$-1 mM MgCl$_2$ (VBS+Me$^{++}$) were prepared as described by Chase (M. W. Chase, in "Methods in Immunology and Immunochemistry," Vol. II, C. A. Williams and M. W. Chase, eds., Academic Press, New York, 1968, p. 388).

Sodium phosphate buffer, 47 mM, pH 7.4, containing 1 mM EDTA was prepared as described by Taylor et al (P. Taylor, S. Fink, D. H. Bing and R. H. Painter, J. Immunol. 118, 1722-1727 [1977]).

EDTA buffer, 100 mM, pH 7.4; 0.1 mole of Na$_2$H$_2$ EDTA.H$_2$O was dissolved in distilled H$_2$O per liter of buffer and adjusted to pH 7.4 with 4 M NaOH prior to dilution to final volume.

Diamine buffer, pH 7.4; 1 mole of NaCl, 0.2 mole of 1,3-diaminopropane (free base) and 0.2 mole of H$_3$BO$_3$ were added per liter of buffer, the pH was adjusted to 7.4 with 12 N HCl prior to dilution to final volume (D. H. Bing, J. M. Andrews, F. L. Suddath and R. Spencer, in "Protides of Biological Fluids," H. Peeters, ed., Pergamon Press, New York, 1975, pp. 551-557).

Tris buffer, pH 8.1, 0.1 ionic strength; 20.86 grms Tris(hydroxymethyl)aminomethane and 100 ml of 1 N HCl were mixed and diluted to 1 liter (M. W. Chase, in "Methods in Immunology and Immunochemistry," Vol. II, C. A. Williams and M. W. Chase, eds., Academic Press, New York, 1968, p. 404).

All chromatography was performed at 4° C. DEAE ion exchange chromatography was performed as described by Taylor et al (P. Taylor, S. Fink, D. H. Bing and R. H. Painter, J. Immunol. 118, 1722-1727 [1977]), except linear gradients consisting of increasing NaCl concentrations were used to develop the chromatogram. Approximately 1 gram of resin was used per mg of protein chromatographed and a flow rate of 50 to 60 ml/hour was maintained. The total volume of the gradient was 5 to 6 times the bed volume of the resin.

ACA-22 Ultragel was used for gel filtration. A column 2.5×100 cm was used for 50 to 60 mg of protein and 5 ml fractions collected at a rate of 5 ml/hour. The diamine buffer was the running buffer.

Affinity chromatography on (IGG)-(p-azo-benzyloxyethylsulfonoethoxy)-(Sepharose CL-4B) (azo-IgG-Sepharose) was done as described by Assimeh et al (S. N. Assimeh, D. H. Bing and R. H. Painter, J. Immunol. 113, 225–234 [1974]), except 100 mM EDTA, pH 7.4, was used to elute the Clr-Cls pool and the diamine buffer was used to elute the Clq pool. The flow rate was maintained at 50 to 60 ml/hour.

Affinity chromatography of Clq on IgG-Sepharose was done as described by Sledge and Bing (C. R. Sledge and D. H. Bing, J. Immunol. 111, 661–666 [1973]), except the diamine buffer was used to elute the Clq. One ml of IgG-Sepharose resin was used per mg of protein in the Clq pool obtained from the IgG-azo-Sepharose resin.

Immunoelectrophoresis was performed in 1% agarose at pH 8.6. The chamber buffers contained pH 8.6 Veronal buffer with an applied voltage of 6 volts/cm (C. A. Williams, in "Methods in Immunology and Immunochemistry," Vol. III, C. A. Williams and M. W. Chase, eds., Academic Press, New York, 1971, p. 237). Electroimmunoassay was performed as described by Laurell (C. B. Laurell, Anal. Biochem. 10, 358–362 [1965]). In both cases, gels were washed overnight in 1.0 M NaCl to remove unprecipitated protein, dried and stained with 1% amido black in 7.5% acetic acid and 5% methanol in $H_2O$.

SDS-polyacrylamide gel electrophoresis was performed in 10% slab gels as described by Laemmli (U. K. Laemmli, Nature 227, 680–685 [1970]). Protein bands were stained with 0.025% Coomassie Brilliant Blue R250 prepared in 10% acetic acide 15% methanol in $H_2O$ (v/v/v). Proteins in 0.1% SDS were reduced in 20 mM dithiothreitol at 37° for 60 minutes, followed by alkylation in 40 mM iodoacetamide for 30 minutes at 37°, and 1 minute in a boiling water bath prior to electrophoresis. Unreduced samples were alkylated with 40 mM iodoacetamide. Standards for SDS-PAGE were as follows: spectrin (MW=240,000 and 220,000), phosphorylase a (MW=94,000), human serum albumin (MW=68,000), glutamic dehydrogenase (MW=56,000), creatine kinase (MW=40,000), horse myoglobin (MW=29,000). All proteins were obtained from Sigma and treated identically to the Clq, Clr and Cls samples.

IgG-p-azo-benzyloxyethylsulfonoethoxy-Sepharose CL-4B [IgG—(p)—N=N—$C_6H_4$—$CH_2$-$H_2$—$SO_2$—$CH_2CH_2$—O—Sepharose CL-4B] of the preferred embodiment was prepared as follows: One liter of Sepharose was filtered and washed with 2 liter of distilled $H_2O$. The resin was added to 1000 ml of 1 M sodium carboate, pH 11.0, and diluted to 1800 ml in the pH 11, 1 M $Na_2CO_3$. 200 gm of divinylsulfone (DVS, Aldrich) was added and allowed to react for 20 minutes with stirring. The resin was filtered and washed quickly with 1 liter of 1 M sodium carbonate, pH 11.0. To this was added immediately 40 grams p-nitrobenzylalcohol dissolved in 100 ml acetone plus 500 ml of 50% aqueous dimethylformamide. The mixture was allowed to react 8 hours with stirring at room temperature, and then filtered and washed with 2 liters of 50% aqueous dimethylformamide followed by 2 liters of methanol and then 1 liter 0.5 M $NaHCO_3$, pH 8.5. The resin was suspended in 300 ml of 0.5 M $NaHCO_3$, pH 8.5, and reduced at 40° C. for 1 hour with stirring by adding dry sodium dithionite to a final concentration of 0.2 M. It was then filtered and washed with 1 liter each pH 8.5, 0.5 M $NaHCO_3$, distilled $H_2O$, and finally 0.5 N HCl. It was then suspended in 500 ml ice cold 0.5 N HCl, 500 ml of ice cold 0.1 M $NaNO_2$ added and stirred 7 minutes on ice. The diazo resin was then filtered and washed on a cold funnel with 1000 ml ice cold 0.5 N HCl, 1000 ml ice cold distilled $H_2O$ and suspended in 400 ml of ice cold pH 8.5 0.1 M $NaHCO_3$. Next, 5 grams of IgG, in 400 ml of ice cold pH 8.5, 0.1 M $NaHCO_3$ was added and the pH adjusted to 8.5 with ice cold 4 N NaOH. The mixture was allowed to react overnight at 4° C. with stirring. Non-bound protein was removed by filtering and washing with 2 liters each of 0.15 M NaCl, 3 M NaCl, 0.2 M $Na_2H_2$ EDTA, pH 7.4, and diamine buffer. All reactions except the overnight coupling at 4° C. were done in a fume hood. Based on protein determinations by the biuret reaction (O. H. Lowry, N. J. Rosebrough, A. L. Farr and R. J. Randall, J. Biol. Chem. 193, 265–275 [1951]), 3.16 grams of IgG were bound to 550 ml of settled resin.

Anti Cls and anti-Clr Sepharose resins were prepared by coupling the 23% $Na_2SO_4$ fraction of goat anti-Clr or anti-Cls antiserum to CNBr activated Sepharose. The CNBr activation was performed as described by March et al ((S. C. March, I. Parikh and P. Cuatrecasas, Anal. Biochem. 60, 149–152 [1974]). Amino acid analysis was performed on 100 to 200 μg samples hydrolyzed at 110° for 24, 48 and 72 hours in 6 N HCl in vacuo. For Clr and Cls, the samples were previously reduced in the presence of 0.1 M mercaptoethanol (redistilled) for 6 hours at 37° under nitrogen in the presence of 500 mM Tris-Hcl-100 mM EDTA buffer-6 M guanidine hydrochloride, pH 8.7. The samples were adjusted to pH 9.0 and alkylated overnight with a 12-fold molar excess of recrystallized iodoacetic acid. They were then dialyzed exhaustively against water and the protein concentration determined by the Lowry biuret reaction (O. H. Lowry, N. J. Rosebrough, A. L. Farr and R. J. Randall, J. Biol. Chem. 193, 265–275 [1951]). There was no detectable cysteine in any of the samples. Clq samples were dialyzed against water, an equal volume of 12 N HCl added, and hydrolyzed 24 hours at 110° in vacuo. Cysteine was measured as half cysteine. Total carbohydrate was determined by the procedure which uses anthrone reagent, as described by Spiro (R. G. Spiro, in "Methods in Enzymology," Vol. III, E. F. Neufeld and U. Ginsburg, eds., Academic Press, New York 1966, pp. 4–5). In each case all samples were dialyzed into water and protein concentration determined by the Lowry biuret procedure (O. H. Lowry, N. J. Rosebrough, A. L. Farr and R. J. Randall, J. Biol. Chem. 193, 265–275 [1951]). A Beckman 121C Amino Acid Analyzer was used. Tryptophan was determined spectrophotometrically, (T. W. Goodwin and R. A. Morton, Biochem. J. 40, 628–635 [1946], H. Edelboch, Biochemistry 6, 1948–1954 [1967]).

Initial immunochemical analysis of the various Cohn fractions prepared by the Biologic Laboratories of the Massachusetts State Laboratory Institute revealed that the Clq was roughly 8 times normal plasma levels in Cohn Fraction I and 6 times normal plasma levels in Fraction II and III. Analysis of Cohn I for Cl hemolytic activity confirmed that functional Cl was present in Fraction I at 8 to 10 times normal plasma levels, and about normal plasma levels in Fractions II and III. Cohn I and Cohn II and III were prepared as described (L. E. Strong, in "Encyclopedia of Chemical Technology," Vol. 2, R. E. Kirk and D. F. Othmar, eds., Interscience Encyclopedia, New York, 1948, pp. 1–29). They were obtained as dry powders, resolubilized in 0.15 M NaCl and insoluble material removed by centrifugation. The clear supernatants were assayed. As the purification procedure is based on the ability to bind the Cl complex to IgG bound to a resin, the Cohn Fraction I was chosen as starting material, where the Clq and Cl activity coincided. A further consideration which led to choosing Fraction I was the lower plasminogen and Cl inhibitor content in this fraction (58% and 25% of normal plasma levels, respectively). The former leads to activation and proteolysis of Clr and Cls, whereas the latter binds irreversibly to and inhibit Clr and Cls (J. M. Andres and R. D. Baillie, J. Immunol. 123, 1403–1408 [1979], G. B. Naff and O. D. Ratnoff, J. Exp. Med. 12, 571–593 [1968], N. R. Cooper, Thromb. Haemost. 42, 262 [1979], P. C. Harpel and N. R. Cooper, in "Proteases and Biological Control," E. Reich, D. Rifkin and E. Shaw, eds., Cold Spring Harbor, N.Y., 1973, pp. 387–405, K. B. M. Reid, R. M. Lowe and R. R. Porter, Biochem. J. 130, 749–763 [1972]). Thus, the presence of these proteins could lead to lower yields and/or inactive products during the course of purification.

Turning now to the purification steps using the resin of this invention, the Figure is a flow sheet of the isolation of Clq, Clr and Cls. The objective in the design of the flow scheme was to minimize the chances for nonspecific proteolysis and denaturation by removing, as quickly as possible, the unwanted proteins. The purification process is described as follows:

Step 1

Fresh (less than 24 hours after Sharples centrifugation) Cohn Fraction I paste (8 to 10 kg) was cut into approximately 4 cm cubes and extracted for 18 hours with 8 to 10 liters of 0.5 M NaCl. This was accomplished by stirring at 4° C. in 14 liter Nalgene plastic carboys with overhead stirrers and stainless steel paddles (Caframo; Fisher Scientific).

Step 2

The solid material was removed by filtration through five layers of cheese cloth. The yield of filtrate was about one-half the initial volume of the 0.5 NaCl. The filtrate was dialyzed against 10 volumes of veronal buffered saline (VBS) containing 10 mM $CaCl_2$ for 18 hours at 4° C. This resulted in formation of a solid clot which was broken up by brief (5 seconds at low speed) homogenization in a commercial Waring blender with a capacity of 4 liters. The solid material was removed by filtration through cheese cloth and discarded. The volume at this point was about two-thirds of that which it was in the previous step.

Step 3

$CaCl_2$ was added to a final concentration of 10 mM and the filtrate stirred 1 to 2 hours at 4° C. Insoluble material and any additional clot was removed by centrifugation (9,000× g) for 30 minutes at 4° C.

Step 4

The clear supernatant was immediately added to IgG-azo-Sepharose at a ratio approximately 2:1 (v/v) and the mixture stirred 12 to 18 hours at 4° C. in a 14 liter Nalgene plastic carboy with a magnetic stirrer. Ten kg of Cohn I paste yielded about 3 liters of extract at this point, which required 1.5 liters of resin. The IgG-azo-Sepharose had been previously equilibrated with pH 7.4 VBS-1 mM $CaCl_2$.

Step 5

After incubation at 4° C., the unbound protein was removed from the resin by filtering it on a Buchner funnel (S&S #526 filter paper, Schleicher & Schuell, Keene, New Hampshire) and washing with pH 7.4 VBS-1 mM $CaCl_2$ until the $A_{280}$ of the filtrate was 0.2 to 0.1.

Step 6

The resin was then suspended in a minimum volume of buffer and poured into a 5×100 cm column, washed in the column until $A_{280}=0.1$. The crude Clr-Cls pool was eluted with 100 mM EDTA, pH 7.4, followed by elution of the crude Clq pool with the pH 7.4 diamine buffer.

Step 7

Both pools were concentrated in Amicon cells containing PM30 membranes. The Clr and Cls were resolved by chromatography on DEAE cellulose. The Clq was purified by affinity chromatography on IgG-Sepharose as described by Sledge and Bing (C. R. Sledge and D. H. Bing, J. Immunol. 111, 661–666 [1973]), modified as described above.

Step 8

Analysis by SDS-PAGE, immunoelectrophoresis and the electroimmunoassay always showed that the Clq, Clr and Cls obtained in Step 7 were contaminated with other proteins to the extent of 5 to 10%. In the case of Clq, the main contaminant was IgG or IgM; for Clr it was Cls, and for Cls it was Clr. To achieve final purification, each fraction was subjected to a final step. Clq was purified by gel filtration on ACA-22 Ultragel, a product of LKB Inc., New Jersey. Clr was purified by rechromatography on DEAE and then adsorption with an antiCls antibody resin. In most cases, final purification of Cls was accomplished by rechromatography on DEAE, although on occasion it was necessary to remove the residual Clr with anti-Clr Sepharose. The conditions for rechromatography on DEAE were identical to those used in the initial separation of Clr and Cls, except the size of the column and total volume of the gradient was reduced to accommodate the smaller amount of protein. For adsorption on anti-Clr and anti-Cls resin, 0.2 mg of protein was applied per ml of resin and the non-adsorbed protein applied to the column was washed through in pH 7.4, 47 mM $NaPO_4$-1.0 mM NaCl-1 mM EDTA. This chromatography was done at 25° and 30 ml plastic syringes used to hold the resins.

The degree of purification of Clq, Clr and Cls was estimated by immunochemical determination of the Clq, Clr and Cls concentrations in relationship to total protein content. These data are summarized in Table I. It can be seen that the greatest purification step is the affinity chromatography step.

TABLE I

Yields and Cl Activity of Clq, Clr and Cls Purified from Cohn Fraction I

| Fraction | Protein, mg | Clq (mg[d]) | Clr (mg[d]) | Cls (mg[d]) | NZTP[c] units/mg | no additions | Cl Titer[a] reconstituted[b] |
|---|---|---|---|---|---|---|---|
| 1. Cohn paste, 6.2 kg | — | | | | — | | — |
| 2. 0.5 M NaCl Extract | 250,000 | 550 | 650 | 513 | ND | $5.9 \times 10^6$ | — |
| 3. Non-adsorbed | 200,000 | 20 | 315 | 234 | ND | $0.009 \times 10^6$ | — |
| 4. 0.1 M EDTA Eluent | 2,450 | 10 | 310 | 250 | 650 | $0.016 \times 10^6$ | — |
| 5. Diamine Eluent | 370 | 350 | 10 | 10 | 150 | 0 | — |
| 5. + 6. | ND | ND | ND | ND | ND | — | $0.16 \times 10^6$ |
| 6. Clq | 215 | 215 | 0 | 0 | 0 | 9.4 | $1.3 \times 10^6$ |
| 7. Clr | 167 | 0 | 167 | 0 | 530 | 63 | $9.0 \times 10^4$ |
| 8. Cls | 191 | 0 | 0 | 191 | 1932 | 176 | $8.3 \times 10^4$ |

[a]Titer = Z × dilution as measured with EAC4, C2 and CEDTA.
[b]The titer of each component is determined in the presence of excess of the other two.
Clq— 2.15 mg/ml, Clr— 1.0 mg/ml, Cls— 2.63 mg/ml.
[c]between 1 and 10 μg of protein was assayed. One unit is defined as 1 nmole of para-nitrophenol released per ml in 5 minutes from 30 μM NZTP at 23° at pH 8.1.
[d]Determinde by electroimmunoassay.

The results of the present study verify that large quantities of highly purified Clq, Clr and Cls can be isolated from Cohn Fraction I. Several precautions are taken using the material. First the extraction of a Cohn Fraction I takes place within 24 hours of its collection in the fractionation process and the temperature is maintained as close to 4° C. as reasonable. Preferably plasma from which the Cohn Fraction I is derived is tested to be sure that it is free of hepatitis B antigen. The work is done as quickly as possible to remove the desired fractions early to avoid the possibility of inactivation due to proteolysis or other unknown inactivating material.

The affinity chromatographic steps are important to this purification scheme. As the data in Table I show, all of the Cl activity is removed in the first affinity step. The chemical nature of this resin is important. If the IgG is not present, no adsorption and no fractionation occurs. The chemical "arm" is equally important, as similar fractionation on IgG-Sepharose results in no such resolution of Clr-Cls from Clq. The azo-IgG resin of this invention is very stable. There seems to be little loss of the bound IgG, and these resins maintain their ability to fractionate Cl over a period of several months. Usually within six months, however, the matrix does break down, presumably due to loss of the bead structure as a result of the constant stirring and filtering. This is in contrast to the IgG-p-azo-benzamido ethylaminoethyl-Sepharose orginally described, (S. N. Assimeh, D. H. Bing and R. H. Painter, J. Immunol. 113, 225–234 [1974]), which could be used only for 3 to 4 runs before it lost its ability to fractionate Cohn Fraction I. The second affinity step in the purification scheme described in this report does use the IgG-Sepharose resin preparated by direct CNBr activation (C. R. Sledge and D. H. Bing, J. Immunol. 111, 661–666 [1973]). Although the IgG-p-azo-benzyloxyethylsulfonoethoxy-Sepharose can be used in this step, the resolution of Clq on IgG-Sepharose is sharper, with less contaminating IgG. It is found that inclusion of diamine in the buffer is desirable for quantitative elution of the Clq from either resin, in contrast to the results of Kolb et al (W. P. Kolb, L. M. Kolb and E. R. Podack, J. Immunol. 122, 2103–2111 [1979]) who used 1 M NaCl to elute Clq from IgG-Sepharose. This could be due to the different methodology they used to activate the Sepharose with CNBr or perhaps due to the different nature of the starting material (clotted plasma, as opposed to Cohn Fraction I).

The usefulness of the technique of this invention is demonstrated by the quality and yields of purified protein. Based on the concentrations of Clq, Clr and Cls in the 0.5 M NaCl extract, estimated overall yield of Clq, Clr and Cls is 39%, 25% and 37%, respectively. The degree of purification of each from the 0.5 M NaCl extract can also be estimated from the immunochemical determinations. For Clq, Clr and Cls, this was 454, 384 and 487, respectively. Estimates of degree of purification based on activity are difficult, as there is a great deal of NZTP esterase activity in the Cohn Fraction I which is not Clr and Cls. Evaluation of Clq activity in terms of effective molecules per μg indicates that the activity of this material ($7.1 \times 10^9$ effective molecules/μg) is comparable with Clq purified by other methods, see review by Kolb et al (W. P. Kolb, L. M. Kolb and E. R. Podack, J. Immunol. 122, 2103–2111 [1979]). The biochemical purity of Clr and Cls is demonstrated by the activity with respect to synthetic substrates. The Cls has 85% of the theoretical enzymatic activity based on the $V_{max}$ of this enzyme for NZTP. The Clr was 75% active by active site titration with NpGB. In fact, this is a low estimate, as purified Clr aggregates, which results in an underestimate in activity (J. M. Andrews and R. D. Baillie, J. Immunol. 123, 1403–1408 [1979]).

Finally, based on the amino acid analysis and molecular weight analysis by SDS-PAGE, the purified Clq, Clr and Cls obtained from Cohn Fraction I are similar to the same proteins isolated from clotted plasma or serum. There is no evidence for any degradation as a result of the extraction process or proteolysis. As shown here and in other studies (J. M. Andrews and R. D. Baillie, J. Immunol. 123, 1403–1408 [1979]) immunoadsorption of residual Clr or Cls from Cls and Clr, respectively, removes the 5% contaminating proteins detected in the functional assay. Based on these results, these proteins appear suitable for structural studies, as well as use in such tests as immune complex assays or investigations of the biochemical activities of the complement proteins.

I claim:

1. A resin capable of separating Clq, Clr and Cls from fluids comprising a protein selected from the class consisting of IgG, IgM and Fc fragments thereof having linked thereto at at least one histidine site thereof an organic arm, said arm comprising a polysaccharide linked to said protein by a portion having the following formula:

B—N=N—C₆H₄—(CH₂)ₙ—X—(CH₂)₂—R—(CH₂)₂—X-polysaccharide n=1,2, 3 or 4

X=O or NH

R=SO₂ or CH₂NHCH₂ or:

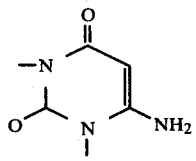

or:
[—CH(OH)CONHCH₂]₂— or:
—CH₂NHCONHCH₂—

B=IgG, IgM or Fc fragments.

2. A resin in accordance with the resin of claim 1 wherein said protein is attached to said polysaccharide by azo-benzyloxyethylsulfonoethoxy.

3. A resin in accordance with the resin of claim 1 and further comprising said polysaccharide being an agarose polymer.

4. A resin in accordance with the resin of claim 1 and further comprising said polysaccharide being a polygalactose.

5. A resin in accordance with the resin of claim 1 and further comprising said polysaccharide being a polyglucose.

6. In a method of forming a resin in accordance with claim 1,
the steps of linking a polysaccharide to a backbone of protein IgG, IgM of Fc fragments thereof by activating the polysaccharide to react by causing a reaction to take place with a diallene followed by reaction with an aromatic nitro compound and forming a diazonium ion,
coupling said diazonium ion at a temperature below 4° C. with said protein at histidine sites thereof at a pH of from 8 to 9.

7. Immunoglobulin linked to polysaccharide resin by an arm having the following formula:

—N=N—C₆H₄—CH₂—O—(CH₂)₂—SO₂—(CH₂)₂—O—.

8. A method in accordance with the method of claim 6 wherein said resin is immunoglobulin linked to polysaccharide resin by an arm having the following formula:

—N=N—C₆H₄—CH₂—O—(CH₂)₂—SO₂—(CH₂)₂—O—.

* * * * *